(12) United States Patent  (10) Patent No.: US 8,728,103 B2
Surti et al.  (45) Date of Patent: May 20, 2014

(54) LINEAR CLAMPS FOR ANASTOMOSIS (75) Inventors: Vihar Surti, Winston-Salem, NC (US); Tyler McLawhorn, Winston-Salem, NC (US); Richard W. Ducharme, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 371 days.

(21) Appl. No.: 12/779,378

(22) Filed: May 13, 2010

(65) Prior Publication Data
US 2010/0331866 A1 Dec. 30, 2010

Related U.S. Application Data

(60) Provisional application No. 61/220,848, filed on Jun. 26, 2009.

(51) Int. Cl.
*A61B 17/11* (2006.01)

(52) U.S. Cl.
USPC .......................................... 606/153

(58) Field of Classification Search
CPC .............. A61B 17/11; A61B 17/1114; A61B 2017/1139
USPC ......... 606/153–156, 151, 157, 213, 215, 216, 606/221; 24/455, 485, 487–488, 530–531
See application file for complete search history.

(56) References Cited

U.S. PATENT DOCUMENTS

| | | |
|---|---|---|
| 3,299,883 A | 1/1967 | Rubens |
| 3,358,676 A | 12/1967 | Frei et al. |
| 3,674,014 A | 7/1972 | Tillander |
| 3,709,214 A | 1/1973 | Robertson |
| 4,022,208 A | 5/1977 | Valtchev |
| 4,214,587 A | 7/1980 | Sakura, Jr. |
| 4,899,744 A | 2/1990 | Fujitsuka et al. |
| 5,081,997 A | 1/1992 | Bosley et al. |
| 5,234,447 A | 8/1993 | Kaster et al. |
| 5,297,536 A | 3/1994 | Wilk |
| 5,346,501 A | 9/1994 | Regula et al. |
| 5,391,156 A | 2/1995 | Hildwein et al. |

(Continued)

FOREIGN PATENT DOCUMENTS

| | | |
|---|---|---|
| DE | 197 04 211 | 8/1998 |
| EP | 1077047 A2 | 2/2001 |

(Continued)

OTHER PUBLICATIONS

International Search Report and Written Opinion of International Search Authority for PCT/US2010/053514 dated Dec. 6, 2010.

(Continued)

*Primary Examiner* — Julian W Woo
*Assistant Examiner* — Shaun L David
(74) *Attorney, Agent, or Firm* — Brinks Gilson & Lione (57) ABSTRACT

The present embodiments provide medical apparatuses, systems, and methods for rapidly forming an anastomosis between two viscera. The medical apparatus generally comprises two bases with two clamp members rotatably attached to the bases, the clamp members being capable of compressing tissue. The system generally comprises positioning and then deploying the medical apparatus between and within two stomas via an elongate member. The method generally comprises using the medical system to create an anastomosis between the stomach and the jejunum.

23 Claims, 8 Drawing Sheets

(56) References Cited

U.S. PATENT DOCUMENTS

| | | | |
|---|---|---|---|
| 5,429,131 A | 7/1995 | Scheinman et al. | |
| 5,458,131 A | 10/1995 | Wilk | |
| 5,554,183 A | 9/1996 | Nazari | |
| 5,562,683 A | 10/1996 | Chan | |
| 5,562,688 A | 10/1996 | Riza | |
| 5,571,090 A | 11/1996 | Sherts | |
| 5,571,119 A | 11/1996 | Atala | |
| 5,573,540 A | 11/1996 | Yoon | |
| 5,573,543 A | 11/1996 | Akopov et al. | |
| 5,578,044 A | 11/1996 | Gordon et al. | |
| 5,582,615 A | 12/1996 | Foshee et al. | |
| 5,584,835 A | 12/1996 | Greenfield | |
| 5,586,986 A | 12/1996 | Hinchcliffe | |
| 5,593,414 A | 1/1997 | Shipp et al. | |
| 5,630,824 A | 5/1997 | Hart | |
| 5,643,292 A | 7/1997 | Hart | |
| 5,643,317 A | 7/1997 | Pavcnik et al. | |
| 5,645,552 A | 7/1997 | Sherts | |
| 5,653,717 A | 8/1997 | Ko et al. | |
| 5,665,067 A | 9/1997 | Linder et al. | |
| 5,667,527 A | 9/1997 | Cook et al. | |
| 5,674,231 A | 10/1997 | Green et al. | |
| 5,683,402 A | 11/1997 | Cosgrove et al. | |
| 5,690,656 A | 11/1997 | Cope et al. | |
| 5,693,060 A | 12/1997 | Martin | |
| 5,695,525 A | 12/1997 | Mulhauser et al. | |
| 5,700,273 A | 12/1997 | Buelna et al. | |
| 5,728,113 A | 3/1998 | Sherts | |
| 5,728,116 A | 3/1998 | Rosenman | |
| 5,741,278 A | 4/1998 | Stevens | |
| 5,746,751 A | 5/1998 | Sherts | |
| 5,779,720 A | 7/1998 | Walder-Utz et al. | |
| 5,788,625 A | 8/1998 | Plouhar et al. | |
| 5,792,153 A | 8/1998 | Swain et al. | |
| 5,810,848 A | 9/1998 | Hayhurst | |
| 5,824,010 A | 10/1998 | McDonald | |
| 5,836,955 A | 11/1998 | Buelna et al. | |
| 5,836,956 A | 11/1998 | Buelna et al. | |
| 5,846,253 A | 12/1998 | Buelna et al. | |
| 5,860,990 A | 1/1999 | Nobis et al. | |
| 5,865,791 A | 2/1999 | Whayne et al. | |
| 5,865,836 A | 2/1999 | Miller | |
| 5,868,763 A | 2/1999 | Spence et al. | |
| 5,873,530 A | 2/1999 | Chizinsky | |
| 5,891,159 A | 4/1999 | Sherman et al. | |
| 5,902,228 A | 5/1999 | Schulsinger et al. | |
| 5,908,428 A | 6/1999 | Scirica et al. | |
| 5,919,184 A | 7/1999 | Tilton, Jr. | |
| 5,931,844 A | 8/1999 | Thompson et al. | |
| 5,938,668 A | 8/1999 | Scirica et al. | |
| 5,947,997 A | 9/1999 | Pavcnik et al. | |
| 5,948,000 A | 9/1999 | Larsen et al. | |
| 5,951,531 A | 9/1999 | Ferdman et al. | |
| 5,968,078 A | 10/1999 | Grotz | |
| 5,972,002 A | 10/1999 | Bark et al. | |
| 5,976,159 A | 11/1999 | Bolduc et al. | |
| 5,984,949 A | 11/1999 | Levin | |
| 6,007,515 A | 12/1999 | Epstein et al. | |
| 6,015,414 A | 1/2000 | Werp et al. | |
| 6,021,776 A | 2/2000 | Allred et al. | |
| 6,030,365 A | 2/2000 | Laufer | |
| 6,059,749 A | 5/2000 | Marx | |
| 6,077,217 A | 6/2000 | Love et al. | |
| 6,086,608 A | 7/2000 | Ek et al. | |
| 6,110,183 A | 8/2000 | Cope | |
| 6,113,612 A | 9/2000 | Swanson et al. | |
| 6,149,658 A | 11/2000 | Gardiner et al. | |
| 6,152,935 A | 11/2000 | Kammerer et al. | |
| 6,152,937 A | 11/2000 | Peterson et al. | |
| 6,156,006 A | 12/2000 | Brosens et al. | |
| 6,159,223 A | 12/2000 | Danks et al. | |
| 6,171,321 B1 | 1/2001 | Gifford, III et al. | |
| 6,183,486 B1 | 2/2001 | Snow et al. | |
| 6,193,732 B1 | 2/2001 | Frantzen et al. | |
| 6,200,329 B1 | 3/2001 | Fung et al. | |
| 6,251,116 B1 * | 6/2001 | Shennib et al. | 606/153 |
| 6,290,674 B1 | 9/2001 | Roue et al. | |
| 6,293,952 B1 | 9/2001 | Brosens et al. | |
| 6,293,961 B2 | 9/2001 | Schwartz et al. | |
| 6,319,271 B1 | 11/2001 | Schwartz et al. | |
| 6,328,727 B1 | 12/2001 | Frazier et al. | |
| 6,348,059 B1 | 2/2002 | Hathaway et al. | |
| 6,355,050 B1 | 3/2002 | Andreas et al. | |
| 6,368,300 B1 | 4/2002 | Fallon et al. | |
| 6,402,765 B1 | 6/2002 | Monassevitch et al. | |
| 6,419,669 B1 | 7/2002 | Frazier et al. | |
| 6,423,087 B1 | 7/2002 | Sawada | |
| 6,428,550 B1 | 8/2002 | Vargas et al. | |
| 6,494,889 B1 | 12/2002 | Fleischman et al. | |
| 6,527,753 B2 | 3/2003 | Sekine et al. | |
| 6,535,764 B2 | 3/2003 | Imran et al. | |
| 6,569,173 B1 | 5/2003 | Blatter et al. | |
| 6,572,629 B2 | 6/2003 | Kalloo et al. | |
| 6,689,062 B1 | 2/2004 | Mesallum | |
| 6,811,555 B1 * | 11/2004 | Willis et al. | 606/153 |
| 6,918,871 B2 | 7/2005 | Schulze | |
| 7,128,708 B2 | 10/2006 | Saadat et al. | |
| 7,232,448 B2 | 6/2007 | Battles et al. | |
| 7,273,451 B2 | 9/2007 | Sekine et al. | |
| 7,351,202 B2 | 4/2008 | Long | |
| 7,431,694 B2 | 10/2008 | Stefanchik et al. | |
| 7,585,308 B2 | 9/2009 | Weisenburgh, II et al. | |
| 7,591,828 B2 | 9/2009 | Ortiz | |
| 7,608,086 B2 | 10/2009 | Tanaka et al. | |
| 7,618,427 B2 | 11/2009 | Ortiz et al. | |
| 7,637,919 B2 | 12/2009 | Ishikawa et al. | |
| 7,654,951 B2 | 2/2010 | Ishikawa | |
| 7,666,197 B2 | 2/2010 | Orban, III | |
| 7,691,103 B2 | 4/2010 | Fernandez et al. | |
| 7,708,748 B2 | 5/2010 | Weisenburgh, II et al. | |
| 7,713,278 B2 | 5/2010 | Hess et al. | |
| 7,725,214 B2 | 5/2010 | Diolaiti | |
| 2001/0049497 A1 | 12/2001 | Kalloo et al. | |
| 2002/0022851 A1 | 2/2002 | Kalloo et al. | |
| 2003/0088256 A1 * | 5/2003 | Conston et al. | 606/155 |
| 2003/0216613 A1 | 11/2003 | Suzuki et al. | |
| 2003/0225312 A1 | 12/2003 | Suzuki et al. | |
| 2004/0087985 A1 | 5/2004 | Loshakove et al. | |
| 2004/0092975 A1 | 5/2004 | Loshakove et al. | |
| 2004/0097801 A1 | 5/2004 | Mesallum | |
| 2004/0225191 A1 | 11/2004 | Sekine et al. | |
| 2004/0249367 A1 | 12/2004 | Saadat et al. | |
| 2005/0004584 A1 | 1/2005 | Franco et al. | |
| 2005/0101837 A1 | 5/2005 | Kalloo et al. | |
| 2005/0107664 A1 | 5/2005 | Kalloo et al. | |
| 2005/0277965 A1 | 12/2005 | Brenneman et al. | |
| 2005/0277981 A1 | 12/2005 | Maahs et al. | |
| 2006/0025654 A1 | 2/2006 | Suzuki et al. | |
| 2006/0025788 A1 | 2/2006 | Loshakove et al. | |
| 2006/0036267 A1 | 2/2006 | Saadat et al. | |
| 2006/0100480 A1 | 5/2006 | Ewers et al. | |
| 2006/0167482 A1 | 7/2006 | Swain et al. | |
| 2006/0178560 A1 | 8/2006 | Saadat et al. | |
| 2006/0200004 A1 | 9/2006 | Wilk | |
| 2006/0211919 A1 | 9/2006 | Wilk | |
| 2006/0212063 A1 | 9/2006 | Wilk | |
| 2006/0229653 A1 | 10/2006 | Wilk | |
| 2006/0237022 A1 | 10/2006 | Chen et al. | |
| 2006/0237023 A1 | 10/2006 | Cox et al. | |
| 2006/0241344 A1 | 10/2006 | Wilk | |
| 2006/0241480 A1 | 10/2006 | Wilk | |
| 2006/0241570 A1 | 10/2006 | Wilk | |
| 2006/0241651 A1 | 10/2006 | Wilk | |
| 2006/0241691 A1 | 10/2006 | Wilk | |
| 2006/0252997 A1 | 11/2006 | Wilk | |
| 2006/0253123 A1 | 11/2006 | Wilk | |
| 2006/0258909 A1 | 11/2006 | Saadat et al. | |
| 2006/0264986 A1 | 11/2006 | Park et al. | 606/153 |
| 2006/0287666 A1 | 12/2006 | Saadat et al. | |
| 2006/0293701 A1 | 12/2006 | Ainsworth et al. | 606/153 |
| 2007/0004958 A1 | 1/2007 | Ohdaira | |
| 2007/0051380 A1 | 3/2007 | Pasricha | |
| 2007/0100375 A1 | 5/2007 | Mikkaichi et al. | |
| 2007/0100376 A1 | 5/2007 | Mikkaichi et al. | |

(56) References Cited

U.S. PATENT DOCUMENTS

| | | |
|---|---|---|
| 2007/0106313 A1 | 5/2007 | Golden et al. |
| 2007/0112362 A1 | 5/2007 | Mikkaichi et al. |
| 2007/0123840 A1 | 5/2007 | Cox |
| 2007/0163585 A1 | 7/2007 | Uesugi et al. |
| 2007/0163596 A1 | 7/2007 | Mikkaichi et al. |
| 2007/0163604 A1 | 7/2007 | Mikkaichi et al. |
| 2007/0167675 A1 | 7/2007 | Miyamoto et al. |
| 2007/0167676 A1 | 7/2007 | Miyamoto et al. |
| 2007/0167967 A1 | 7/2007 | Mikkaichi et al. |
| 2007/0173859 A1 | 7/2007 | Mikkaichi et al. |
| 2007/0173867 A1 | 7/2007 | Brenneman ............... 606/153 |
| 2007/0197864 A1 | 8/2007 | Dejima et al. |
| 2007/0198000 A1 | 8/2007 | Miyamoto et al. |
| 2007/0198033 A1 | 8/2007 | Kalloo et al. |
| 2007/0208360 A1 | 9/2007 | Demarais et al. |
| 2007/0213702 A1 | 9/2007 | Kogosaka et al. |
| 2007/0213749 A1 | 9/2007 | Kogosaka et al. |
| 2007/0213750 A1 | 9/2007 | Weadock |
| 2007/0219411 A1 | 9/2007 | Dejima et al. |
| 2007/0225734 A1 | 9/2007 | Bell et al. |
| 2007/0255100 A1 | 11/2007 | Barlow et al. |
| 2007/0255165 A1 | 11/2007 | Uesugi et al. |
| 2007/0255273 A1 | 11/2007 | Fernandez et al. |
| 2007/0255295 A1* | 11/2007 | Starkebaum et al. ......... 606/142 |
| 2007/0260214 A1 | 11/2007 | Mikkaichi et al. |
| 2007/0270629 A1 | 11/2007 | Charles |
| 2008/0015408 A1 | 1/2008 | Paolitto et al. |
| 2008/0021277 A1 | 1/2008 | Stefanchik |
| 2008/0064921 A1 | 3/2008 | Larkin et al. |
| 2008/0064927 A1 | 3/2008 | Larkin et al. |
| 2008/0064931 A1 | 3/2008 | Schena et al. |
| 2008/0065097 A1 | 3/2008 | Duval et al. |
| 2008/0065098 A1 | 3/2008 | Larkin |
| 2008/0065099 A1 | 3/2008 | Cooper et al. |
| 2008/0065100 A1 | 3/2008 | Larkin |
| 2008/0065101 A1 | 3/2008 | Larkin |
| 2008/0065102 A1 | 3/2008 | Cooper |
| 2008/0065103 A1 | 3/2008 | Cooper et al. |
| 2008/0065104 A1 | 3/2008 | Larkin et al. |
| 2008/0065105 A1 | 3/2008 | Larkin et al. |
| 2008/0065106 A1 | 3/2008 | Larkin |
| 2008/0065107 A1 | 3/2008 | Larkin et al. |
| 2008/0065108 A1 | 3/2008 | Diolaiti |
| 2008/0065109 A1 | 3/2008 | Larkin |
| 2008/0065110 A1 | 3/2008 | Duval et al. |
| 2008/0071288 A1 | 3/2008 | Larkin et al. |
| 2008/0071289 A1 | 3/2008 | Cooper et al. |
| 2008/0071290 A1 | 3/2008 | Larkin et al. |
| 2008/0071291 A1 | 3/2008 | Duval et al. |
| 2008/0097489 A1 | 4/2008 | Goldfarb et al. |
| 2008/0114378 A1 | 5/2008 | Matsushita |
| 2008/0119868 A1 | 5/2008 | Sharp et al. |
| 2008/0125804 A1 | 5/2008 | Gostout |
| 2008/0154290 A1 | 6/2008 | Golden et al. |
| 2008/0161641 A1 | 7/2008 | Nakazato et al. |
| 2008/0171907 A1 | 7/2008 | Long et al. |
| 2008/0183039 A1 | 7/2008 | Long et al. |
| 2008/0200762 A1 | 8/2008 | Stokes et al. |
| 2008/0208161 A1 | 8/2008 | Kaji et al. |
| 2008/0228029 A1 | 9/2008 | Mikkaichi et al. |
| 2008/0228203 A1 | 9/2008 | Bell et al. |
| 2008/0249416 A1 | 10/2008 | Sato |
| 2008/0275297 A1 | 11/2008 | Bakos et al. |
| 2008/0287963 A1 | 11/2008 | Rogers et al. |
| 2008/0312502 A1 | 12/2008 | Swain et al. |
| 2009/0023985 A1 | 1/2009 | Ewers |
| 2009/0054728 A1 | 2/2009 | Trusty |
| 2009/0054761 A1 | 2/2009 | Voegele et al. |
| 2009/0182195 A1 | 7/2009 | Faller et al. |
| 2009/0221915 A1 | 9/2009 | Voegele et al. |
| 2009/0227828 A1 | 9/2009 | Swain et al. |
| 2009/0254105 A1* | 10/2009 | Thompson ............... 606/153 |
| 2009/0276055 A1 | 11/2009 | Harris et al. |
| 2009/0281559 A1 | 11/2009 | Swain et al. |
| 2010/0010520 A1 | 1/2010 | Takahashi et al. |
| 2010/0036399 A1 | 2/2010 | Viola |
| 2010/0056861 A1 | 3/2010 | Spivey |
| 2010/0063521 A1 | 3/2010 | Manzo |
| 2010/0087842 A1 | 4/2010 | Heinrich et al. |
| 2010/0094319 A1 | 4/2010 | Heinrich et al. |
| 2010/0099947 A1 | 4/2010 | Sato et al. |
| 2010/0113872 A1 | 5/2010 | Asada et al. |
| 2010/0114124 A1 | 5/2010 | Kelleher et al. |
| 2010/0160729 A1 | 6/2010 | Smith et al. |
| 2010/0179510 A1 | 7/2010 | Fox et al. |
| 2010/0179540 A1 | 7/2010 | Marczyk et al. |
| 2010/0198232 A1 | 8/2010 | Diolaiti |

FOREIGN PATENT DOCUMENTS

| | | |
|---|---|---|
| EP | 1493391 A1 | 1/2005 |
| GB | 877903 | 9/1961 |
| WO | WO 98/02316 | 1/1998 |
| WO | WO/2006-121855 | 11/2006 |
| WO | WO 2009/006444 | 1/2009 |

OTHER PUBLICATIONS

Specification Sheet—FUJINON Maximizing Productivity for Double Balloon Endoscopy System (3 pages).

Hagen, et al., Hybrid natural orifice transluminal endoscopic surgery (NOTES) for Roux-en-Y gastric bypass: an experimental surgical study in human cadavers, 2008, pp. 918-924, vol. 40.

Fritscher-Ravens, EUS—Experimental and Evolving Techniques, 2006, pp. S95-S99, vol. 38.

Fritscher-Ravens, et al., Comparative study of NOTES alone vs. EUS-guided NOTES procedures, 2008, pp. 925-930, vol. 40.

Bories, et al., Transgastric endoscopic ultrasonography—guided biliary drainage: results of a pilot study, 2007, pp. 287-291, vol. 39.

Will, et al., Treatment of biliary obstruction in selected patients by endoscopic ultrasonography (EUS)-guided transluminal biliary drainage, 2007, pp. 292-295, vol. 39.

* cited by examiner

LINEAR CLAMPS FOR ANASTOMOSIS

CROSS-REFERENCE TO RELATED APPLICATIONS

This application claims the benefit of U.S. Provisional Patent Application No. 61/220,848 filed on Jun. 26, 2009, entitled "LINEAR CLAMPS FOR ANASTOMOSIS," the entire contents of which are incorporated herein by reference.

FIELD OF THE INVENTION

The present embodiments relate generally to medical apparatuses for forming an anastomosis between two viscera, and more particularly relate to forming a side-to-side anastomosis such as a gastrojejunostomy.

BACKGROUND OF THE INVENTION

Historically, gastrointestinal (GI) surgery has been performed to create a channel between two viscera for the purpose of redirecting bodily fluids, i.e., an anastomosis. It will be recognized that there may be a need to anastomose many different viscera, such as the jejunum and the stomach (gastrojejunostomy), the bile duct and the duodenum, two sections of the small or large intestines, or various other combinations of viscera such as during bariatric surgery.

During surgery to form an anastomosis, the two tissues are often brought together and affixed to one another using fixators such as sutures, staples, or some other fixation means. While fixators are being placed, the tissues of the respective viscera are held in proximity to one another using various means. In open surgery, this is usually accomplished with graspers, forceps, or other tissue holding instruments manipulated by clinicians. In laparoscopic surgery, similar instruments may be used, except the laparotic access limits the number of instruments to a few percutaneous "ports," making the technical challenge of the procedure much greater.

When these types of GI surgery are performed, there exists the potential to breach the mural boundary. Thus, extreme care must be taken to prevent contamination of the pleural and abdominal cavities with GI contents, which are laden with bacteria that do not naturally occur in those locations. If significant contamination occurs, then serious infection can set-in, which can lead to serious illness or death if not treated early and vigorously.

To address some of these limitations and to minimize the invasiveness of such surgeries, magnetic anastomosis devices (MADs) were developed for forming anastomosis. For example, a MAD may consist of two magnet cores surrounded by metal rims. The two magnet cores are positioned in the two viscera between which the anastomosis is desired. Due to the magnetic attraction between the cores, the walls of the two adjacent viscera are compressed. The compression of the walls of the viscera results in ischemic necrosis to produce an anastomosis between the two viscera. When using MADs, it is sometimes necessary to conduct a second procedure to insert a stent or other device to maintain the anastomosis that the MADs created. A second procedure requires additional costs, patient and physician time, and involves certain risks associated with any endoscopic procedure. In addition, when using MADs an anastomosis is created over a several day period, rather than being created immediately at the time of the procedure.

SUMMARY OF THE PREFERRED EMBODIMENTS

The present embodiments provide a medical apparatus, system, and method for rapidly forming an anastomosis between two viscera while reducing the technical challenge and minimizing the potential risk of prior techniques for forming anastomoses. The anastomosis may be formed with surety before the patient leaves the medical facility and eliminates the need for a follow-up procedure. Additional protection against breach of the mural boundary is provided and there is minimal risk of the anastomosis becoming separated or forming a leak while the patient is not in the medical facility.

According to one embodiment, a medical system for approximating the tissues of two viscera includes affixing to an elongate member a medical device that includes two bases with rotatable clamp members attached, and then inserting the medical device through the bodily walls of two viscera. The bases of the medical device are positioned opposite from each other to define an interior space, a longitudinal axis, and a lateral axis. The interior space between the two bases is sized to permit formation of the anastomosis therebetween and to maintain the anastomosis, while the rotatable clamp members compress the two viscera and maintain them in close proximity. The medical device is held to the elongate member and delivered via a first retainer, alternatively two retainers, or holds to the elongate member without a retainer by the nature of its design.

According to more detailed aspects of the medical device, the rotatable clamp members each have a proximal portion and a distal portion that rotate between a delivery state and a deployed state, where the portions are biased toward the deployed state. In the delivery state, the proximal portions rotate away from the distal portions to align longitudinally along the elongate member. In the deployed state, the proximal portions and the distal portions rotate laterally toward each other so that they are proximate to each other.

A method for forming an anastomosis between two viscera is also provided in accordance with the teachings of the present embodiments. Generally, two stomas are created in two viscera, the stomas are brought into proximity with each other, and then the medical device with two bases and rotatable clamp members as described above is provided and is inserted into the stomas. The medical device is positioned within the two viscera such that the proximal portions and the distal portions of the clamp members compress the walls of the two viscera between them and hold the walls proximate to each other.

According to more detailed aspects of the method, the size of the anastomosis may be immediately enlarged by using a knife or other cutting device to excise additional tissue from the walls of the two viscera located within the interior space defined by the rotatable clamp members. The excising step may be performed endoscopically, and the cutting instrument may be introduced through a working channel of an endoscope.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" refers to a direction that is generally towards a physician during a medical procedure, while the term "distal" refers to a direction that is generally away from the medical professional and/or towards a target site within a patient's anatomy during a medical procedure.

Referring now to FIGS. 1 to 4, an embodiment of a medical device 18 is depicted for forming an anastomosis, such as during an endoscopic procedure. As will be discussed herein, the medical device 18 serves to clamp the tissue surrounding the anastomosis, hold it open, as well as facilitate enlargement of the anastomosis. The medical device 18 generally includes a first base 20 and a second base 22 positioned opposite each other along a horizontal axis 29. The bases 20 and 22 are depicted as being semi-circular in shape to correspond to the outer surface of an endoscope, but other shapes are suitable as will be recognized by those skilled in the art. The bases 20 and 22 each have two insert grooves 21 sized to securely receive a first clamp member 28 and a second clamp member 27 attached to the bases 20 and 22 by being pressed into the insert grooves 21. The insert grooves 21 are further depicted in FIG. 4, and include a narrow throat T, preferably formed by one or more projections 21a, so that the clamp members 28 and 27 may be "snap-fit" into the insert grooves 21. The clamp members may also be more permanently attached to the bases 20 and 22, such as by encapsulating them into the bases, or they may attach to the bases via hinges or other fastening devices known in the art.

Figure 1:
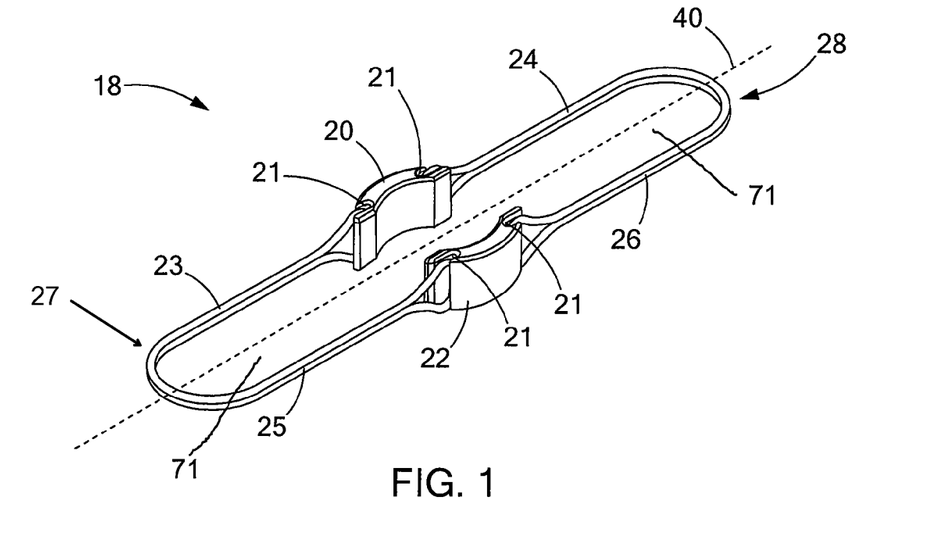
FIG. 1 is a perspective view of one preferred embodiment of a medical device in a deployed state for forming an anastomosis.
Figure 4:
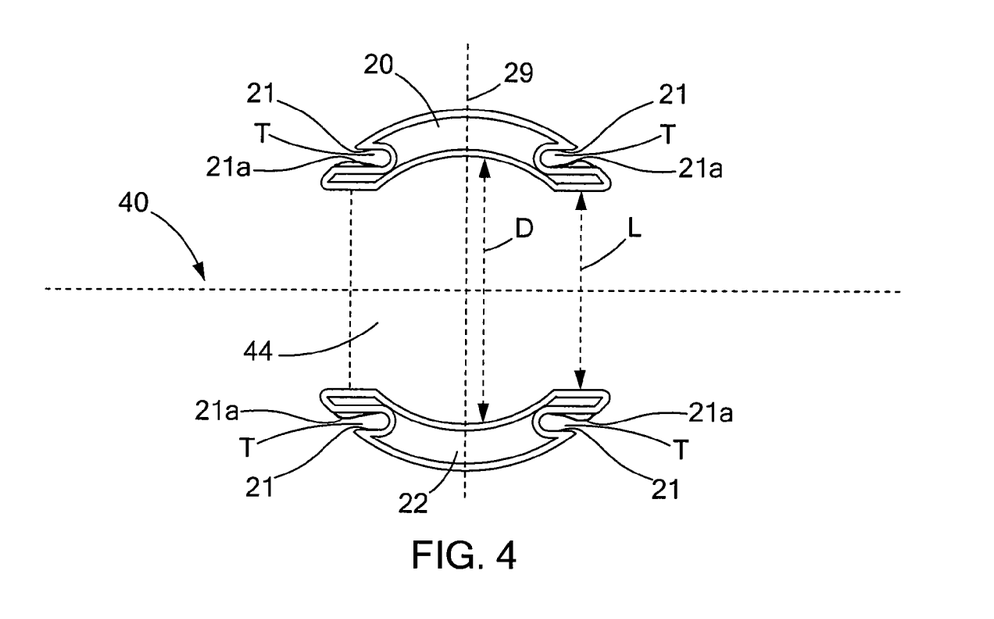
FIG. 4 is a top view of a first base and a second base of the medical device depicted in FIG. 1.

The base 20 is positioned at a distance L opposite from base 22 to define an interior space 44 designed to allow the bases 20 and 22 to fit over an elongate member such as an endoscope. The distance L preferably ranges from about 7 mm to about 20 mm. The diameter D of the interior space may range from about 8 mm to about 23 mm. The dimensions and ranges used herein are generally for endoscopic and gastrointestinal applications, but other sizes for other applications will be readily discernible to those skilled in the art. The bases may be made out of metal, metal alloys, plastics, biocompatible materials, resorbable materials, degradable materials, or any other suitable materials. As used herein, resorbable refers to the ability of a material to be absorbed into a tissue and/or bodily fluid upon contact with the tissue and/or bodily fluid. A number of resorbable materials are known in the art, and any suitable resorbable material may be used. Examples include resorbable homopolymers, copolymers, or blends of resorbable polymers. As used herein, degradable refers to the ability of a material to dissipate upon implantation within a body in a clinically reasonable amount of time, independent of the mechanisms by which dissipation can occur, such as dissolution, degradation, absorption and excretion, and the bases 20 and 22 need only degrade enough such that they disengage from the clamp members 28 and 27. A number of degradable materials are known in the art, and any suitable degradable material may be used. Examples include polyethylene, polypropylene and polyoxypropylene glycolic sugars, as well as polylactic sugars.

Figure 2:
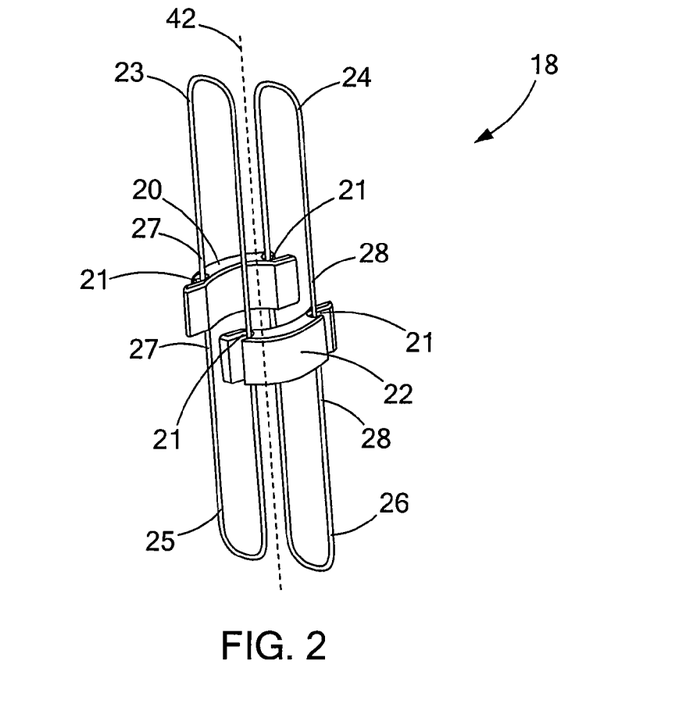
FIG. 2 is a perspective view of the medical device depicted in FIG. 1 in a delivery state.
Figure 3A:
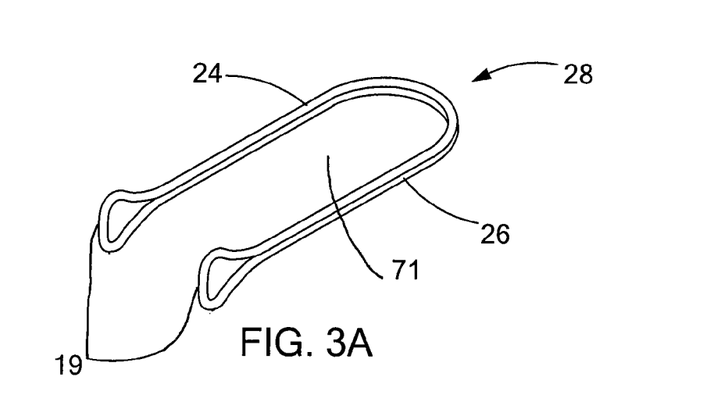
FIG. 3A is a perspective view of a clamp member in a deployed state from the medical device depicted in FIG. 1.

As best seen in FIGS. 1-3A, the first clamp member 28 has a proximal portion 24, an intermediate portion 19 and a distal portion 26. FIG. 3A depicts the unattached first clamp member 28 in its natural state. Both the proximal and distal portions 24 and 26 have a common shape and design such that they can mate as shown in FIG. 1. As depicted, the proximal and distal portions 24 and 26 have a general U-shape, although they could be V-shaped, semi-rectangular in shape, or any other semi-annular shape. The clamp members 28 and 27 thus have a shape that defines an interior space 71 that is in communication with the interior space 44, and preferably contiguous with the interior space 44. The proximal portion 24 and distal portion 26 are rotatable at about the intermediate portion 19 where they attach to the grooves 21 in the bases 20 and 22. Likewise, the second clamp member 27 has a proximal portion 23 and a distal portion 25 that are rotatable at about the intermediate portion 19 where they attach to the grooves 21 in the bases 20 and 22. The clamp members 27, 28 may extend laterally away from the bases 20, 22 a distance ranging from about 4 cm to about 12 cm.

Figure 7:
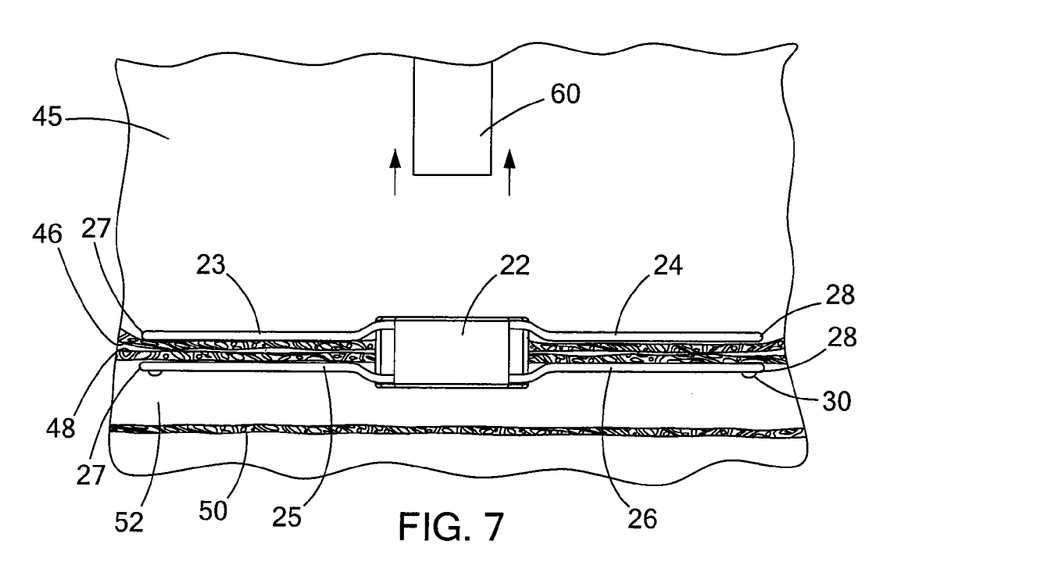
FIG. 7 is a front view similar to FIG. 6 with a medical device for forming an anastomosis deployed in two viscera.
Figure 8:
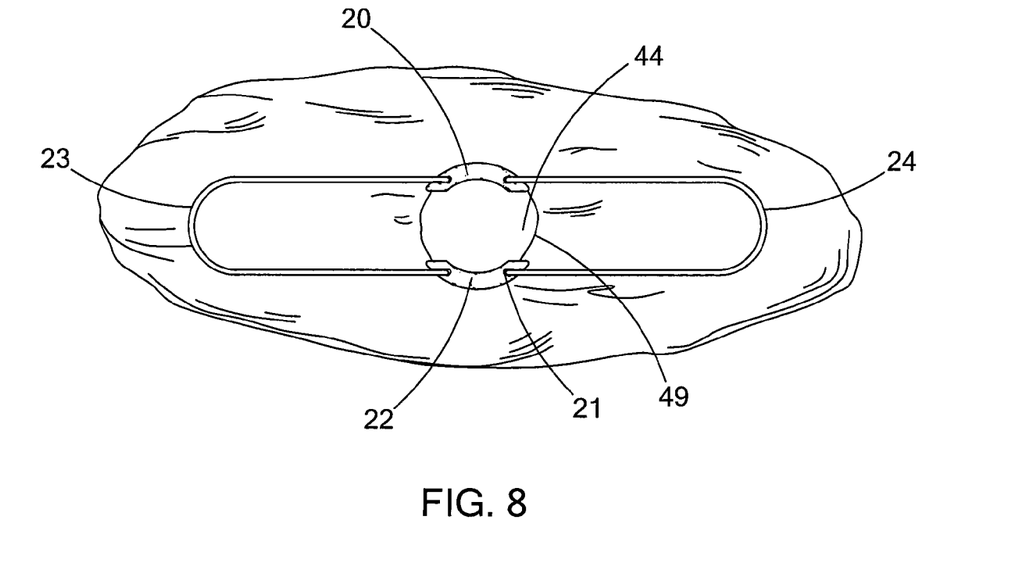
FIG. 8 is a top view of the embodiment of FIG. 1 deployed in tissue.

In FIGS. 1 and 3A, the clamp members 28 and 27 are in a deployed state wherein the proximal portions 24 and 23 have rotated relative to the distal portions 26 and 25 to be about parallel such that the clamp members 28 and 27 project laterally along a lateral axis 40 (about which the bases 20 and 22 are also spaced apart). As used herein, about parallel includes deviations from parallel between the proximal portions 24 and 23 and the distal portions 26 and 25, so long as tissue is capable of being clamped between the proximal portions 24 and 23 and the distal portions 26 and 25. The deployed state may also be described as where the proximal portions 24 and 23 and the distal portions 26 and 25 have rotated so that they are generally perpendicular to the intermediate portion 19, as seen in FIG. 3A. In the deployed state, the proximal portions 24 and 23 have rotated towards the distal portions 26 and 25 to clamp tissue therebetween, as shown in FIG. 7 and described in further detail herein below.

In FIG. 2, the clamp members 28 and 27 of the medical device 18 are in the delivery state wherein the clamp members have rotated toward a longitudinal axis 42 so that the proximal portions 24 and 23 of the clamp members 28 and 27 are adjacent to each other, and the distal portions 26 and 25 of the clamp members 28 and 27 are adjacent to each other. Preferably, the proximal portions 24 and 23 and the distal portions 26 and 25 rotate so that clamp members 28 and 27 are about parallel to each other, aligned along the longitudinal axis 42.

In the embodiment shown in FIGS. 1-3A, the clamp members are biased toward forming the deployed state as depicted in FIG. 3A. The clamp members 28 and 27 are shown as being formed of a metal wire—preferably nitinol—having a round or rectangular (flat) cross-sectional shape, although other constructions may be employed. For example, the clamp members 28 and 27 may be comprised of other metals, metal alloys, plastics, or other materials that have suitable resiliency, whereby the clamp members can rotate according to the natural or imposed shape-memory characteristics of the clamp members. The clamp members 28 and 27 may also be comprised of biocompatible or resorbable materials.

Figure 3B:
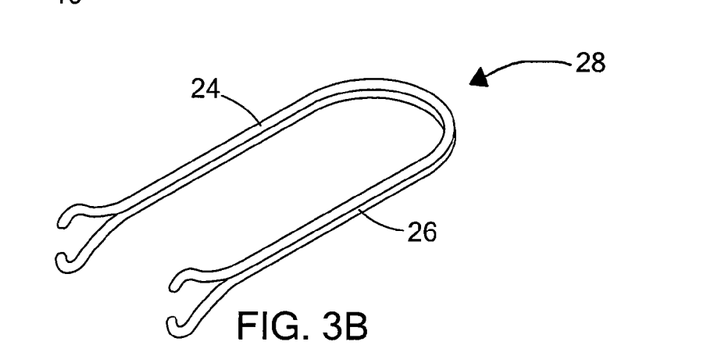
FIG. 3B is a perspective view of an alternative embodiment of a clamp member in a deployed state from the medical device depicted in FIG. 1.

In addition, the clamp members may be attached to the bases by other fastening devices known in the art, or by hinges, springs or other rotatable couplings known in the art. For example, hinges could be biased to rotate the clamp members to the deployed states when the clamp members are not restrained. Moreover, while the clamp members 28 and 27 are depicted as being two solid clamp members in FIGS. 1-3A, each may be made up of two portions, such as two wires, as shown in FIG. 3B. In one embodiment, the proximal portion 24 would be comprised of one wire attached to both bases 20 and 22, the distal portion 26 would be comprised of one wire attached to both bases 20 and 22, and there would not be a connecting intermediate section 19. Hinges (not shown) would rotate the proximal portion 24 toward the distal portion 26 in the deployed state so that each projected laterally away from the bases. Still further, each proximal portion 24 and each distal portion 26 may be made up of two portions (e.g., wires) that have free ends adjacent to each other to form a near contiguous proximal portion 24 and a near contiguous distal portion 26, wherein the clamp member is made up of four rotatable parts (not shown).

A medical system 70 for forming an anastomosis will now be described with reference to FIGS. 5-9. The medical system 70 includes a medical device for forming, creating, and maintaining an anastomosis, an elongate member for delivering the medical device, a retaining device for holding the medical device on the elongate member, and, optionally, an additional pusher device for ejecting the medical device off of the elongate member. According to one embodiment shown in FIG. 5A, the medical device 18 is shown loaded on to an elongate member, in this case an endoscope 60. The endoscope 60 may be any type of scope known in the art, or may alternatively be any flexible elongate member suitable for being inserted into the body for therapeutic purposes. The device 18 is slid over the endoscope 60 to its distal end 43. The distal portions 26 and 25 of the clamp members are held proximate to each other in the delivery state via a first retainer 31. In this embodiment, the first retainer 31 is a suture 32, threaded through an accessory channel 62, which passes through loops or hooks 30 on each distal portion 26 and 25. The suture also may be wrapped around the distal portions 26 and 25 to hold them proximate to each other. Aside from sutures, forceps, a grasper, a clamp, or similar devices known in the art could be threaded through the accessory channel 62 and used to hold the distal portions 26 and 25 proximate to each other, or an elongated cap, a band, or similar devices known in the art could be used to hold the distal portions 26 and 25 proximate to each other.

Figure 5A:
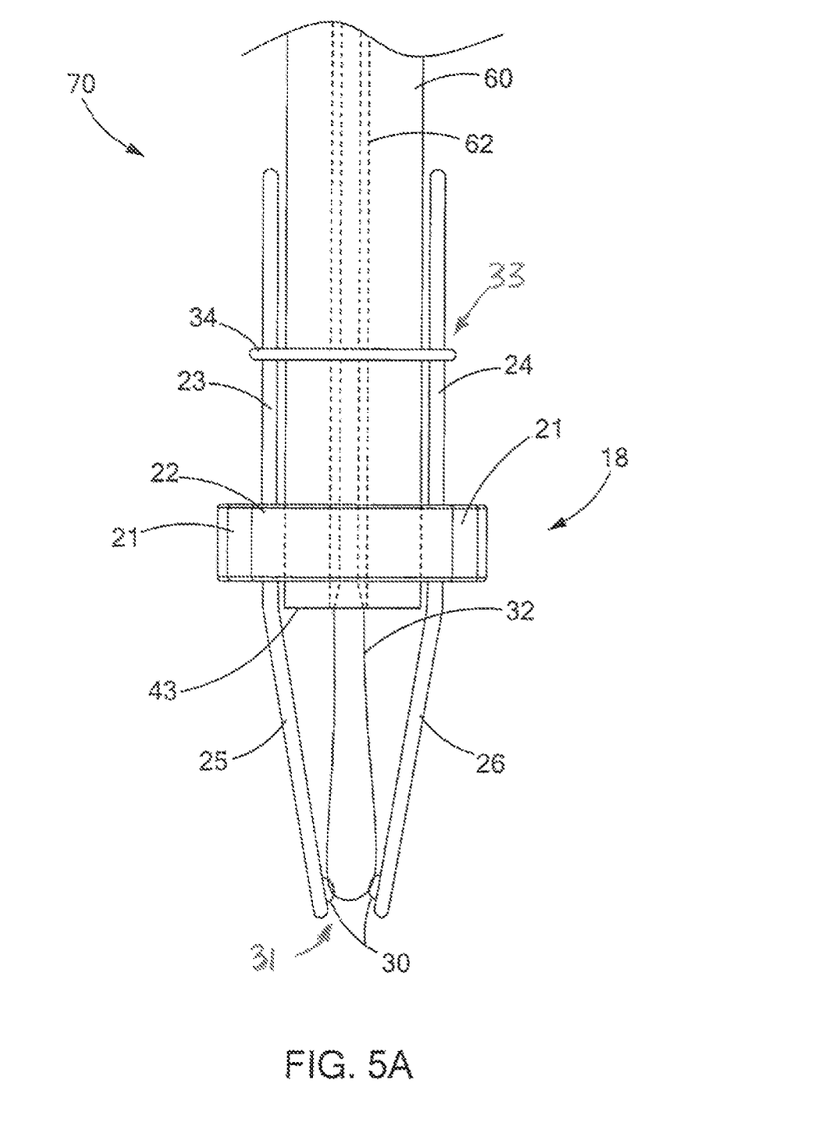
FIG. 5A is a front view of a medical system for creating an anastomosis.
Figure 5B:
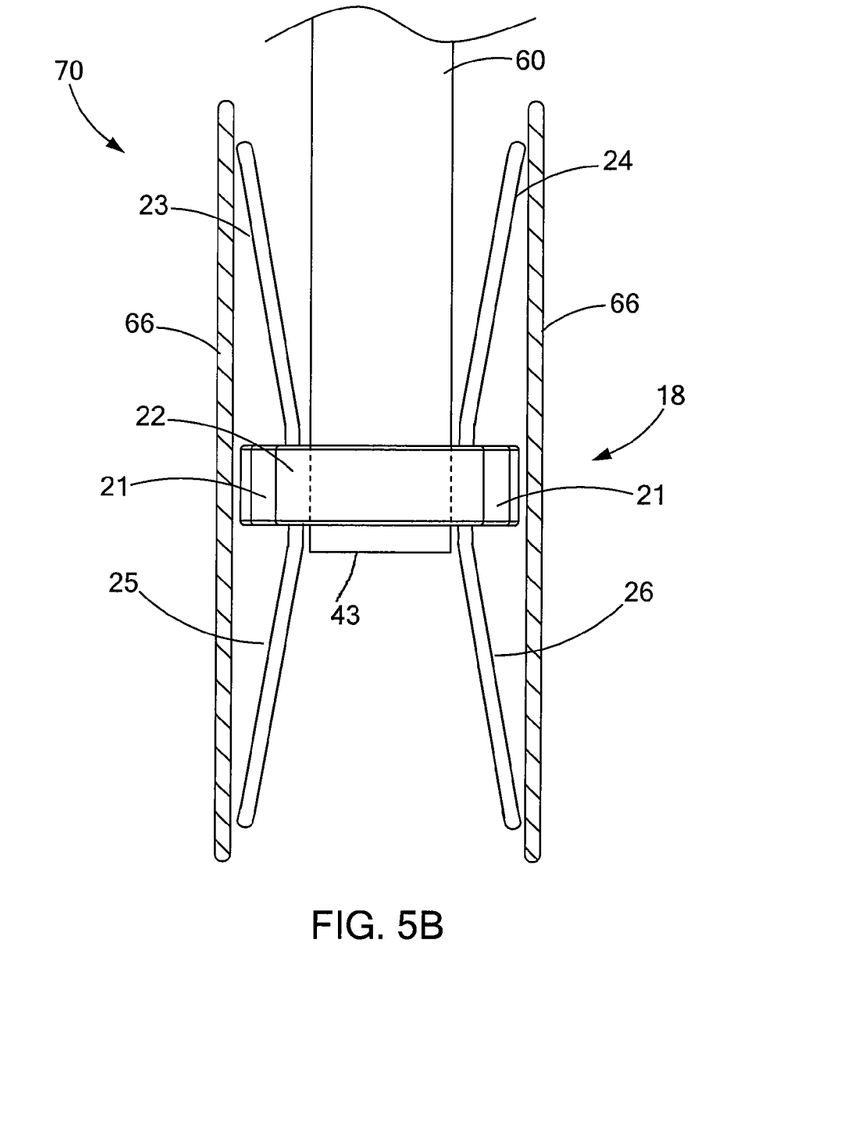
FIG. 5B is a front view, partly in cross-section, of an alternative embodiment of a medical system for creating an anastomosis.
Figure 5C:
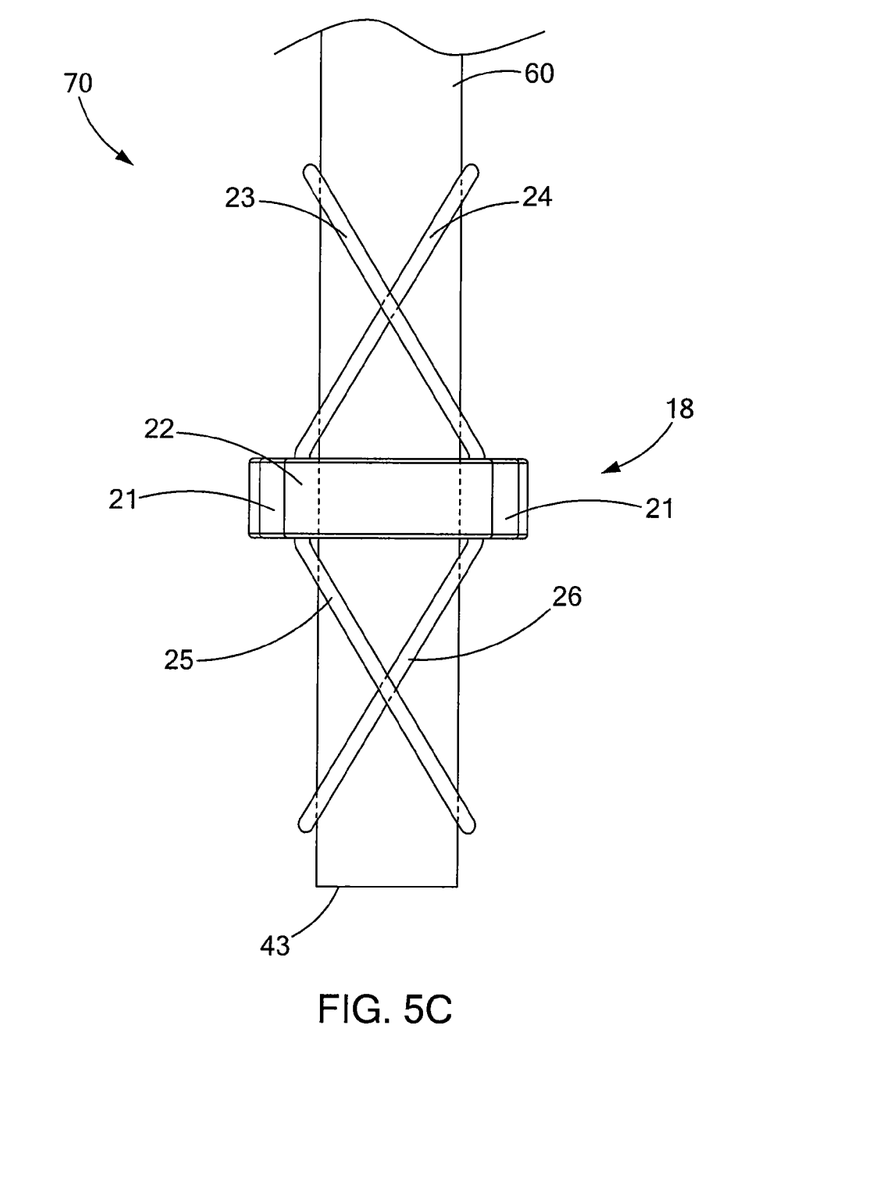
FIG. 5C is a front view of another embodiment of a medical system for creating an anastomosis.

A retainer also holds the proximal portions 24 and 23 in the delivery state and preferably about parallel to each other along the endoscope 60. In this embodiment, a second retainer 33 holds the proximal portions 24 and 23 in the delivery state, and preferably is an elastic band 34. The second retainer 33 may also be a multiband ligator and suture, a clip, a latching mechanism, or other devices known in the art for retaining objects in delivery states. In addition, one retainer, such as an overtube 66 as shown in FIG. 5B, may be used to keep both the distal portions and the proximal portions in place, rather than using the two retainers 31 and 33. Further, the medical device 18 may be configured to retain itself on the endoscope 60 as depicted in FIG. 5C, thereby not needing a retainer. In this manner, the proximal portions 24 and 23 and the distal portions 26 and 25 of the clamp members 28 and 27 would be rotated longitudinally so that the proximal portions 24 and 23 and the distal portions 26 and 25 of the clamp members would all traverse the longitudinal axis 42 with one proximal portion passing through the interior space 71 of the other proximal portion, and one distal portion passing through the interior space 71 of the other distal portion. The medical device 18 would then be fitted over the endoscope 60, and the natural bias of the clamp members to return to the deployed state would cause the clamp members to exert force on the endoscope 60 to maintain the position of the medical device 18 on the endoscope 60.

Figure 6:
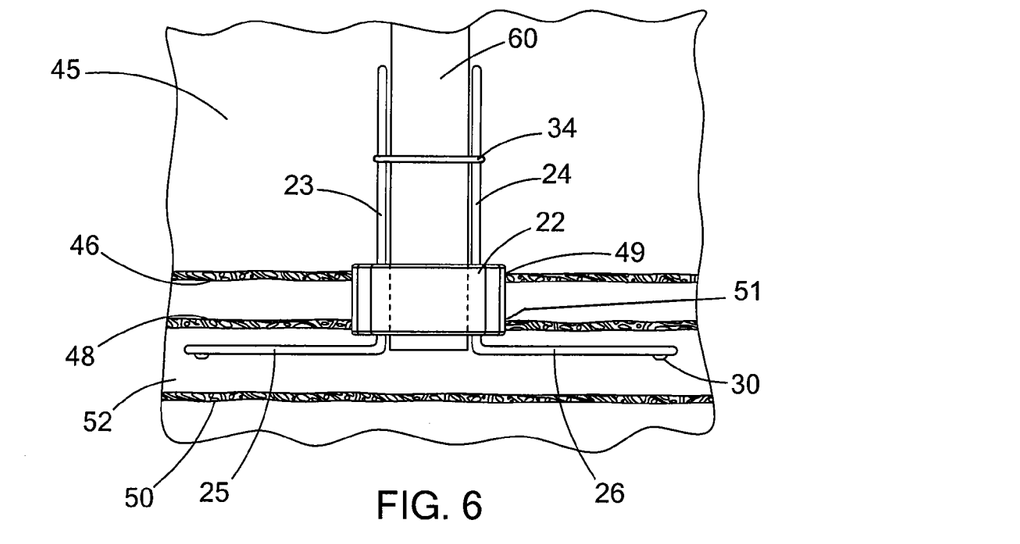
FIG. 6 is a front view of the medical system of FIG. 5A inserted into a cross-sectional view of tissue cut to reveal two viscera.

Referring now to FIG. 6, the medical device 18 has been inserted distally through a stoma 49 of a first bodily wall 46 (e.g., the stomach 45) and through a stoma 51 of a second bodily wall 48 (e.g., the small intestine, and typically, the jejunum 52) to rest within the interior 52 of the jejunum 50. In this embodiment, the suture 32 has been retracted by the clinician or cut and retracted by the clinician, allowing the distal portions 26 and 25 of the clamp members 28 and 27 to rotate to their deployed states. Pulling back (i.e., retracting) the system 70 in the proximal direction causes the distal portions 26 and 25 to exert pressure on the interior surface of the second bodily wall 48.

Referring now to FIG. 7, the endoscope 60 is further retracted until the bases are seen to be at least partially inside a stoma 49 (FIG. 6) of the first bodily wall 46, and the elastic band 34 is released, allowing the proximal portions 24 and 23 to rotate to their deployed states to press against and exert pressure on the proximal side of the first bodily wall 46. The procedure for releasing the proximal portions 24 and 23 varies depending on the retaining device used. When the second retainer 33 is the elastic band 34 as depicted in FIG. 6, then the second retainer 33 can be removed simply by excising the elastic band 34. The endoscope 60 may alternatively be grooved or scored so that retraction of the endoscope 60 engages (e.g. via friction with the scoring) the elastic band 34 so that the elastic band 34 is rolled or moved proximally off of the proximal portions 24 and 23, and preferably remains fixed to the endoscope 60 as it is retracted. Further, a suture may be run down the outside of the endoscope 60 and tied to the second retainer device 33, so that the suture can be pulled to remove the second retainer device 33. Still further, if the overtube 66 is used to cover the entire medical device 18 as depicted in FIG. 5B, then retracting the overtube 66 will first release the distal portions into their deployed states and then will release the proximal portions into their deployed states as the overtube 66 is further retracted. The overtube 66 is sized to receive the scope and apparatus in its lumen. Other retaining devices and means for removing them will be recognized by those skilled in the art.

A medical method for creating an anastomosis will now be described with reference to FIGS. 5-9. Before fully deploying the medical device 18 to create an anastomosis, stomas must be created in the desired viscera, and the stomas must be brought within proximity of each other. One way to achieve this goal would be to load the medical device 18 on an endoscope 60 as depicted in FIG. 5A, 5B, or 5C, and then advance the endoscope to the first viscera. A cutting device (not shown) could be advanced through a working lumen of the endoscope 60 and could be used to create the stoma 49 in the first viscera, for example in the stomach 45. Then the endoscope 60 could be further advanced to the second viscera, such as the jejunum 52, and the cutting device could be used to create a second stoma 51 in the second viscera. The distal portions 26 and 25 of the medical device 18 could be deployed as described above, and then the medical device 18, endoscope 60, and jejunum 52 could be retracted toward the stoma 49 in the first viscera. Once the medical device 18 is properly positioned as it is in FIG. 6, the proximal portions 24 and 23 could be released and the anastomosis would be created.

The stomas may also be created and brought into proximity with one another prior to insertion of the medical device 18. There are numerous ways of achieving this that are known in the art, some of which are described in U.S. Nonprovisional application Ser. No. 12/025,985, filed Feb. 5, 2008, which is incorporated by reference herein in its entirety. Laparoscopic surgery or open surgery and devices used in those types of surgeries may also be employed to create the stomas and to hold them in place proximal to each other to prepare for the insertion of the medical device 18.

Figure 9:
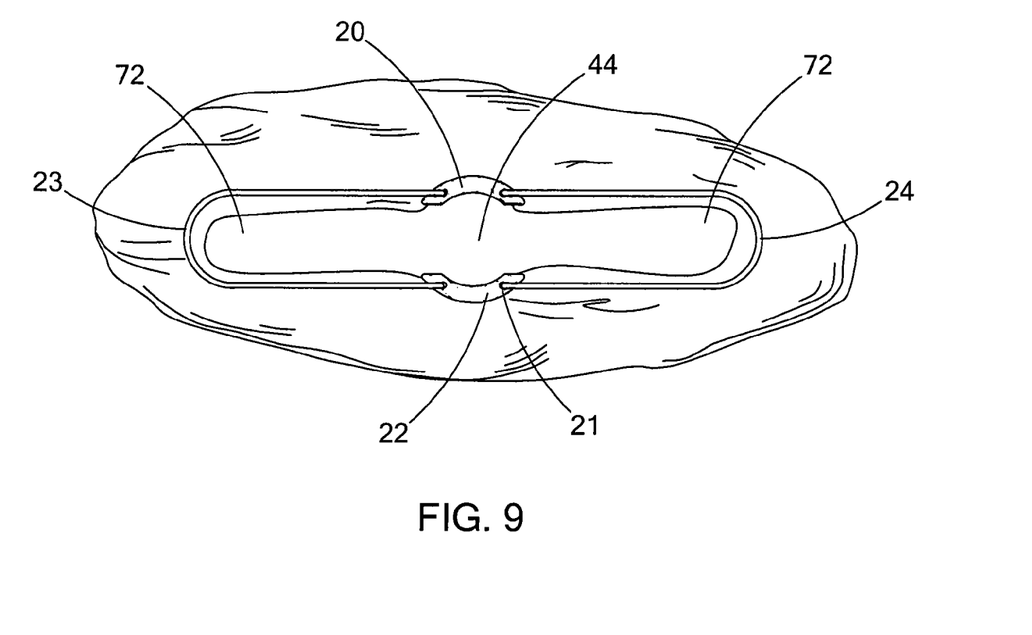
FIG. 9 is a top view of the embodiment of FIG. 1 deployed in tissue where an additional incision has been made to enlarge the anastomosis.

Once the stomas have been created and the medical device 18 has been deployed via the system 70 described above and depicted in FIGS. 5-7, the force exerted by the proximal portions 24 and 23 against the first bodily wall 46 and the force exerted by the distal portions 26 and 25 on the second bodily wall 48 compress the two bodily walls and hold them proximate to each other. The first base 20 and the second base 22 maintain the stoma 49 in the first bodily wall 46 and the stoma 51 in the second bodily wall 48. Thus, the system immediately creates a substantially sized anastomosis. The compression exerted on the bodily walls by the clamp members will result in necrosis of the tissues of the two viscera that are contained between the clamp members, thus resulting in an even larger anastomosis after a few days or a week, depending on the thickness of the tissues and the strength of the material used for the clamp members. If a larger anastomosis is immediately desired, a knife or other cutting device may be used to excise tissue from the two bodily walls by cutting from the interior 44 laterally toward the apex of the first clamp member 28 to create a larger opening 72 as depicted in FIG. 9. Additionally, an incision may be extended laterally from the interior 44 to the apex of the second clamp member 27 to form a second larger opening 72, so that one large, continuous anastomosis is now formed.

Removal of the medical device 18 may be completed through natural means. The pressure exerted on the tissues 46 and 48 will cause necrosis over a number of days, thereby forming an anastomosis that is slightly larger than 24 or 24 and 72 combined. After a certain amount of necrosis occurs, the medical device 18 will dislodge and will pass through the body naturally. Or, the medical device 18 may be made of degradable or resorbable materials so that it will be naturally broken down by the body. In addition, the bases 20 and 22 may be made of a degradable or resorbable material so that they are broken down by the body naturally, and the clamp members 27 and 28 will then pass through the body naturally if they cannot be broken down.

It will be recognized by those skilled in the art that during these anastomosis formation procedures, the area of compression of the tissues 46 and 48 provides a barrier that guards against leakage of the GI contents or other bodily fluids depending on the viscera involved. Likewise, the anastomosis is formed with surety before the patient leaves the medical facility, eliminating the need for a follow-up procedure. Moreover, because the bases 20 and 22—and if an incision is made, the clamp members 28 and 27 also—maintain the size of the anastomosis, there is no need for a second procedure to insert a stent to maintain the opening.

Figure 10:
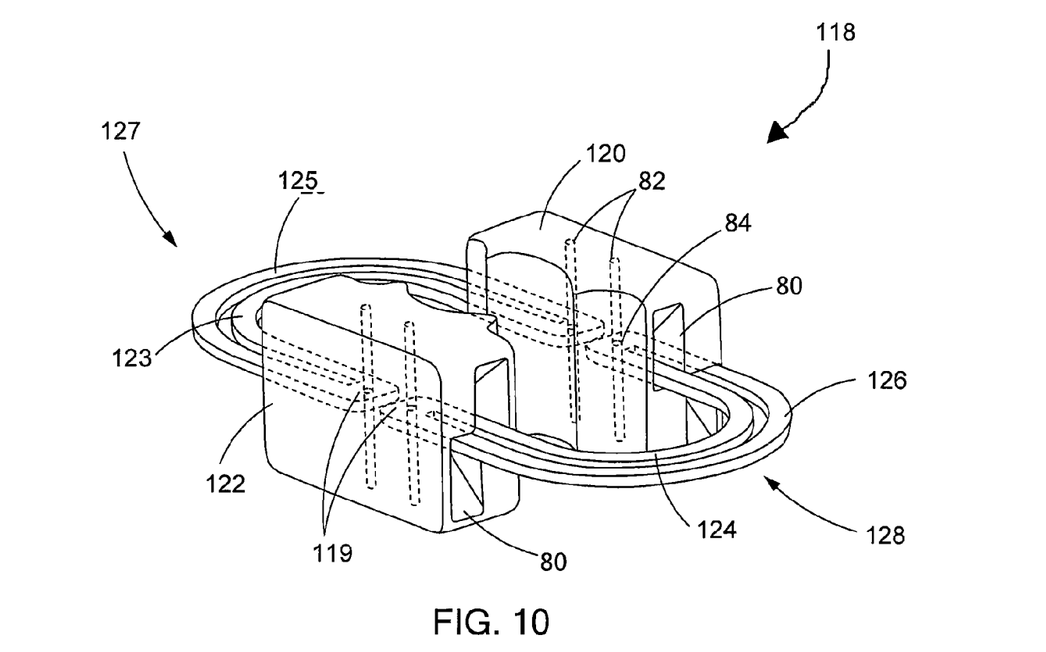
FIG. 10 is a perspective view of another preferred embodiment of a medical device in a deployed state for forming an anastomosis.
Figure 11:
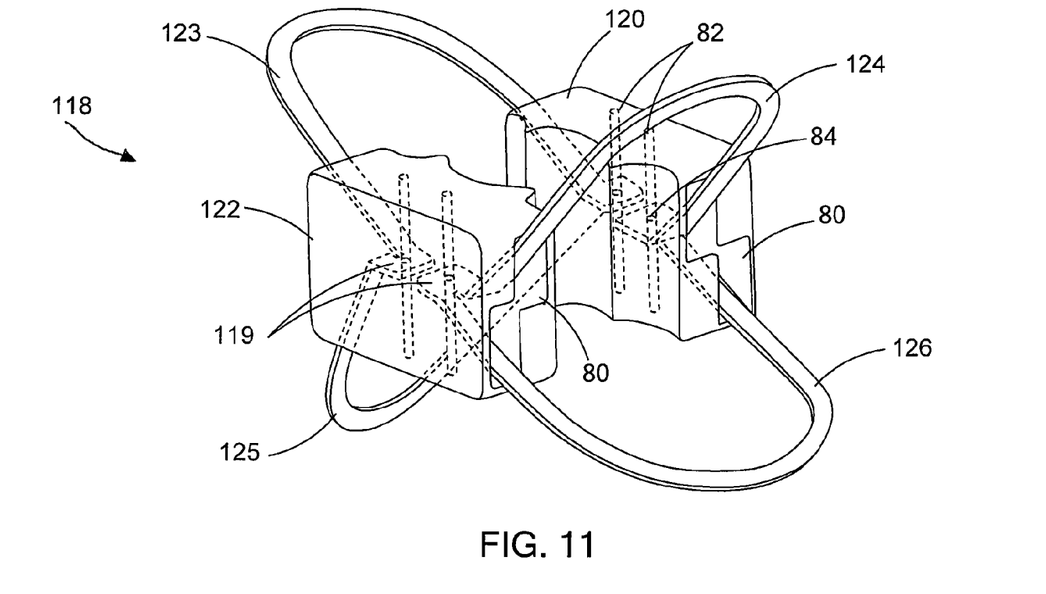
FIG. 11 is a perspective view of the medical device depicted in FIG. 10 in a delivery state.

Referring now to FIGS. 10 and 11, an alternative embodiment of a medical device 118 for forming an anastomosis is depicted. The medical device 118 includes a first base 120 and a second base 122, positioned opposite each other just as in medical device 18. The bases 120 and 122 each have two sockets 80 to receive and guide a first clamp member 128 and a second clamp member 127. In this embodiment, the clamp members 128 and 127 are encapsulated by the bases 120 and 122 and are held in place by cylindrical tubes 82 that pass through insert apertures 84 in each intermediate portion 119. The clamp members may also be attached to the bases 120 and 122 via hinges or other fastening devices known in the art, and changes may be made to the medical device 118 that are generally similar to those previously discussed for medical device 18.

The first clamp member 128 has a proximal portion 124, an intermediate portion 119, and a distal portion 126, and the second clamp member 127 has a proximal portion 123, an intermediate portion 119, and a distal portion 125. FIG. 10 depicts the clamp members 128 and 127 in their natural state, the deployed state. The proximal portions 124 and 123 and the distal portions 126 and 125 are rotatable at about the intermediate portion 119. The dimensions and use of the medical device 118 are generally similar to the medical device 18, and similar modifications to those previously discussed in the prior embodiment can be applied here.

In FIG. 11, the clamp members 128 and 127 of the medical device 118 are in the delivery state wherein the clamp members have rotated longitudinally away from the bases 120 and 122 so that the proximal portions 124 and 123 of the clamp members 128 and 127 are proximate to each other, and the distal portions 126 and 125 are proximate to each other. Sockets 80 in the bases 120 and 122 guide the clamp members from the deployed state to the delivery state and prevent the clamp members 128 and 127 from aligning 180 degrees longitudinally as 28 and 27 of the medical device 18 are capable of doing as depicted in FIG. 2. Although not shown, those of skill in the art will recognize that the sockets 80 and/or the size of the bases 120 and 122 may be modified to allow the clamp members 128 and 127 to rotate 180 degrees longitudinally in the delivery state.

It will be recognized by those skilled in the art that, while the methods described above generally include approximating the bodily walls of two viscera, it will be recognized that the systems, devices, and methods may be used on any two layers of material (e.g., fabrics, cloth, polymers, elastomers, plastics, and rubber) that may or may not be associated with a human or animal body. For example, the systems, devices, and methods can find use in laboratory and industrial settings for approximating two or more layers of material that may or may not find application to the human or animal body, and likewise connecting holes or perforations in two or more layers of material that are not bodily tissue. Some examples include sewing or stitching and related manufacturing, working with synthetic tissues, connecting or repairing polymeric sheets, animal studies, veterinary applications, and post-mortem activities.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An apparatus for facilitating the creation of an anastomosis in bodily tissue, the apparatus comprising:
    a first base positioned opposite from a second base to define an interior space therebetween, the bases and interior space defining a longitudinal axis and a lateral axis, the first and second bases being comprised of a degradable or resorbable material;
    a first clamp member having a proximal portion and a distal portion, the first clamp member being separate and distinct from both bases and attached thereto and projecting laterally therefrom, wherein the proximal portion and the distal portion are rotatable relative to the first and second bases;
    a second clamp member having a proximal portion and a distal portion, the second clamp member being separate and distinct from both bases and attached thereto and projecting laterally therefrom, wherein the proximal portion and the distal portion are rotatable relative to the first and second bases;
    the first and second clamp members each operable between a delivery state and a deployed state, the first and second clamp members being biased towards the deployed state, the deployed state of the first clamp member defining a first interior space in communication with the interior space, and the deployed state of the second clamp member defining a second interior space in communication with the interior space;
    the delivery state of the first clamp member having the proximal portion and the distal portion rotated away from each other, the delivery state of the second clamp member having the proximal portion and the distal portion rotated away from each other; and
    the deployed state of the first clamp member having the proximal portion and the distal portion of the first clamp member in close proximity to each other to hold the bodily tissue therebetween, the deployed state of the second clamp member having the proximal portion and the distal portion of the second clamp member in close proximity to each other to hold the bodily tissue therebetween.

2. The apparatus of claim 1 wherein the first and second clamp members separate upon the material of the first and second bases becoming degraded or resorbed, and wherein the first and second clamp members are sized to separately pass naturally through a gastrointestinal tract of a patient.

3. The apparatus of claim 1 wherein the first and second clamp members each extend laterally away from the first and second bases a distance ranging from about 4 cm to about 12 cm.

4. The apparatus of claim 1 wherein the interior space is adapted to fit over an endoscope.

5. The apparatus of claim 1 wherein the clamp members are comprised of a shape-memory material.

6. The apparatus of claim 1 wherein the first and second clamp members project laterally away from the first and second bases in opposite directions.

7. The apparatus of claim 1 wherein each proximal portion is comprised of one wire and each distal portion is comprised of a separate wire.

8. A medical system comprising the apparatus of claim 1, and further comprising:
    an elongate member defining a longitudinal axis,
    the interior space sized to slidably receive the elongate member;
    a delivery member for ejecting the apparatus off of the elongate member; and
    at least one retainer for maintaining the distal portions of each clamp member in the delivery state and maintaining the proximal portions of each clamp member in the delivery state, the apparatus being held on an exterior of the elongate member in the delivery state such that the relative longitudinal position of the apparatus on the elongate member is maintained during advancement of the elongate member.

9. The medical system of 8 wherein the at least one retainer is a suture.

10. The medical system of claim 8 wherein the at least one retainer is an elastic band.

11. The medical system of claim 8 wherein the at least one retainer is an overtube that maintains the proximal portions and the distal portions of the clamp members in the delivery state.

12. The medical system of claim 8 wherein the proximal and distal portions of both the first and second clamp members are rotated away from each other and beyond the longitudinal axis in their respective delivery states, the elongate member maintaining the position of the proximal and distal portions in their delivery states.

13. The medical system of claim 8 wherein the proximal and distal portions of both the first and second clamp members are semi-annular in shape.

14. The system of claim 8, wherein the first and second bases each have a curved inner surface having a curvature facing the interior space.

15. The system of claim 14, wherein the curvature is semi-circular.

16. The system of claim 8, wherein the apparatus remains generally stationary relative to the elongated member in the delivery state during advancement of the elongate member.

17. The apparatus of claim 1, wherein the proximal portions and distal portions of the first and second clamp members are concentrically arranged in the deployed state.

18. The apparatus of claim 1, wherein the first and second clamp members are formed of material that is not degradable or resorbable.

19. A method of forming an anastomosis, the method comprising the steps of:
    creating a stoma in a first bodily wall;
    creating a stoma in a second bodily wall;
    providing a medical system comprising an apparatus that comprises a first base and a second base with a first and second clamp member attached to the bases, the clamp members having proximal portions and distal portions that are rotatably attached to the bases, the clamp members each having a deployed state wherein the proximal portion of the first clamp member is about parallel to the distal portion of the first clamp member and the proximal portion of the second clamp member is about parallel to the distal portion of the second clamp member, the clamp members each having a delivery state wherein the proximal portion and the distal portion of the first clamp member rotate longitudinally away from each other and the proximal portion and the distal portion of the second clamp member rotate longitudinally away from each other, and the bases adapted to fit over an elongate member;

inserting the apparatus into a bodily lumen;

positioning the distal portions of the first and second clamp members through the stoma in the second bodily wall so that the distal portions are on the distal side of the second bodily wall;

rotating the distal portions of the clamp members from the delivery state to the deployed state wherein the distal portions of the clamp members rotate laterally away from each other to press against an interior surface of the second bodily wall;

rotating the proximal portions of the clamp members from the delivery state to the deployed state wherein the proximal portions of the clamp members rotate laterally away from each other to press against an interior surface of the first bodily wall;

compressing the first and second bodily walls together and holding them proximate to each other after the clamp members have been rotated to the deployed state; and, after compressing the first and second bodily walls together, simultaneously cutting the tissue of the first and second bodily walls to enlarge the size of the stomas.

20. The method of claim 19 wherein the pressure exerted by the clamp members in their deployed states maintains the stoma of the first bodily wall adjacent to the stoma of the second bodily wall.

21. The method of claim 19 wherein the two bases of the apparatus maintain the stomas of the first and second bodily walls.

22. The method of claim 19 wherein the bases are comprised of degradable or resorbable materials.

23. The method of claim 19 wherein the distal portions of the clamp members rotate to the deployed state after releasing a first retainer, and the proximal portions of the clamp members rotate to the deployed state after releasing a second retainer, or alternatively further releasing the first retainer.

* * * * *